(12) United States Patent
Nash

(10) Patent No.: US 6,572,597 B1
(45) Date of Patent: Jun. 3, 2003

(54) THONG PANTY LINER

(76) Inventor: Jennifer M. Nash, 8759 Pine Crest Pl., Rancho Cucamonga, CA (US) 91730

( * ) Notice: Subject to any disclaimer, the term of this patent is extended or adjusted under 35 U.S.C. 154(b) by 0 days.

(21) Appl. No.: 09/887,249

(22) Filed: Jun. 22, 2001

(51) Int. Cl.⁷ .................................................. A61F 13/15
(52) U.S. Cl. .............................. 604/385.05; 604/385.04
(58) Field of Search ...................... 604/385.01, 385.23, 604/385.04, 386, 385.05

(56) References Cited

U.S. PATENT DOCUMENTS

| | | |
|---|---|---|
| D366,524 S | 1/1996 | Chung |
| 5,683,373 A * | 11/1997 | Darby ..................... 604/385.1 |
| 5,713,886 A | 2/1998 | Sturino |
| D392,736 S * | 3/1998 | Erickson .................. D24/125 |
| 5,729,835 A | 3/1998 | Williams |
| D416,324 S | 11/1999 | Nixon |
| D424,195 S | 5/2000 | Talon |
| D425,196 S | 5/2000 | Nixon et al. |
| D445,498 S * | 7/2001 | Renz et al. ................ D24/125 |
| 6,350,258 B1 * | 2/2002 | Markowiecki ....... 604/385.201 |

FOREIGN PATENT DOCUMENTS

WO WO 00/72790 A1 * 12/2000 ........... A61F/13/15

* cited by examiner

*Primary Examiner*—Weilun Lo
*Assistant Examiner*—Jacqueline F Stephens

(57) ABSTRACT

A thong panty liner for protecting a woman while wearing a thong during her menstrual cycle. The thong panty liner includes a layered piece of material having a top layer and a bottom layer and being adapted to securely fasten to a crotch member of a thong; and also includes adhesive being disposed upon a bottom of the bottom layer for securely fastening the layered piece of material to the thong; and further includes a cover member being removably disposed upon the adhesive for the protection thereof.

1 Claim, 2 Drawing Sheets

THONG PANTY LINER

BACKGROUND OF THE INVENTION

1. Field of the Invention

The present invention relates to winged panty liners and more particularly pertains to a new thong panty liner for protecting a woman while wearing a thong during her menstrual cycle.

2. Description of the Prior Art

The use of winged panty liners is known in the prior art. More specifically, winged panty liners heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. No. 5,713,886; U.S. Pat. No. 5,729,835; U.S. Pat. No. Des. 416,324; U.S. Pat. No. Des. 425,196; U.S. Pat. No. Des. 424,195; and U.S. Pat. No. Des. 366,524.

While these devices fulfill their respective, particular objectives and requirements, the aforementioned patents do not disclose a new thong panty liner. The inventive device includes a layered piece of material having a top layer and a bottom layer and being adapted to securely fasten to a crotch member of a thong; and also includes adhesive being disposed upon a bottom of the bottom layer for securely fastening the layered piece of material to the thong; and further includes a cover member being removably disposed upon the adhesive for the protection thereof.

In these respects, the thong panty liner according to the present invention substantially departs from the conventional concepts and designs of the prior art, and in so doing provides an apparatus primarily developed for the purpose of protecting a woman while wearing a thong during her menstrual cycle.

SUMMARY OF THE INVENTION

In view of the foregoing disadvantages inherent in the known types of winged panty liners now present in the prior art, the present invention provides a new thong panty liner construction wherein the same can be utilized for protecting a woman while wearing a thong during her menstrual cycle.

The general purpose of the present invention, which will be described subsequently in greater detail, is to provide a new thong panty liner which has many of the advantages of the winged panty liners mentioned heretofore and many novel features that result in a new thong panty liner which is not anticipated, rendered obvious, suggested, or even implied by any of the prior art winged panty liners, either alone or in any combination thereof.

To attain this, the present invention generally comprises a layered piece of material having a top layer and a bottom layer and being adapted to securely fasten to a crotch member of a thong; and also includes adhesive being disposed upon a bottom of the bottom layer for securely fastening the layered piece of material to the thong; and further includes a cover member being removably disposed upon the adhesive for the protection thereof.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new thong panty liner which has many of the advantages of the winged panty liners mentioned heretofore and many novel features that result in a new thong panty liner which is not anticipated, rendered obvious, suggested, or even implied by any of the prior art winged panty liners, either alone or in any combination thereof.

It is another object of the present invention to provide a new thong panty liner which may be easily and efficiently manufactured and marketed.

It is a further object of the present invention to provide a new thong panty liner which is of a durable and reliable construction.

An even further object of the present invention is to provide a new thong panty liner which is susceptible of a low cost of manufacture with regard to both materials and labor, and which accordingly is then susceptible of low prices of sale to the consuming public, thereby making such thong panty liner economically available to the buying public.

Still yet another object of the present invention is to provide a new thong panty liner which provides in the apparatuses and methods of the prior art some of the advantages thereof, while simultaneously overcoming some of the disadvantages normally associated therewith.

Still another object of the present invention is to provide a new thong panty liner for protecting a woman while wearing a thong during her menstrual cycle.

Yet another object of the present.invention is to provide a new thong panty liner which includes a layered piece of material having a top layer and a bottom layer and being adapted to securely fasten to a crotch member of a thong; and also includes adhesive being disposed upon a bottom of the bottom layer for securely fastening the layered piece of material to the thong; and further includes a cover member being removably disposed upon the adhesive for the protection thereof.

Still yet another object of the present invention is to provide a new thong panty liner that is easy and convenient to use.

Even still another object of the present invention is to provide a new thong panty liner that is securely held in place and doesn't slide and move about upon the crotch member of the thong.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
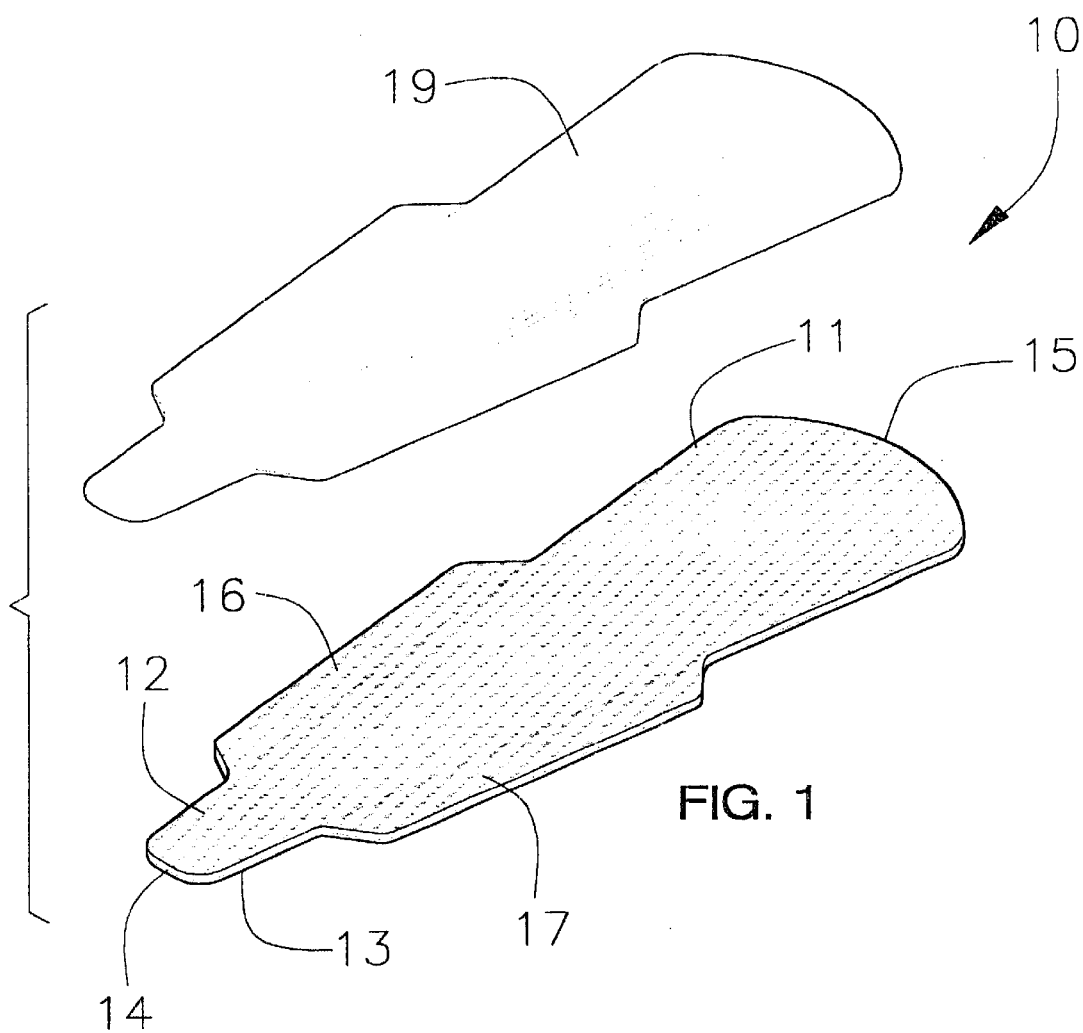
FIG. 1 is an exploded perspective view of a new thong panty liner according to the present invention.
Figure 2:
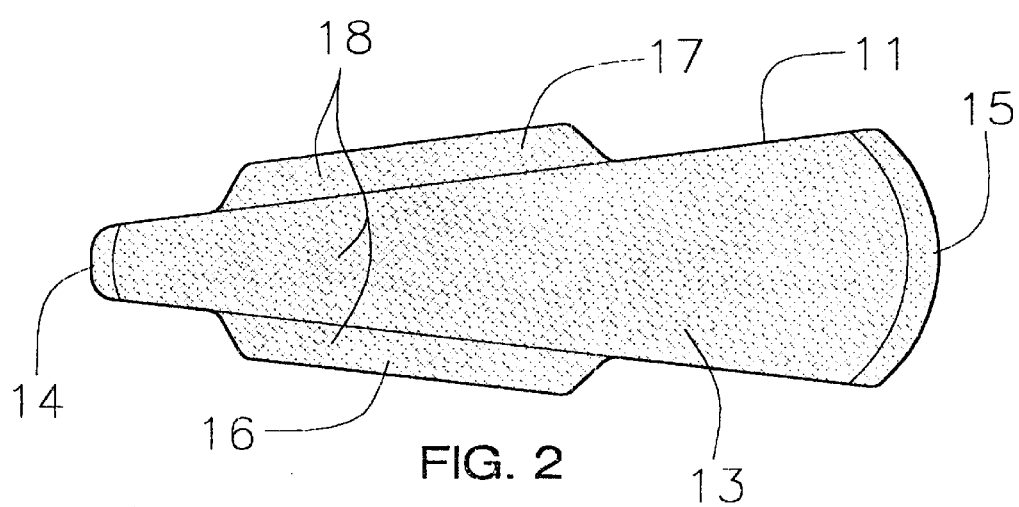
FIG. 2 is a bottom plan view of the layered piece of material of the present invention.
Figure 3:
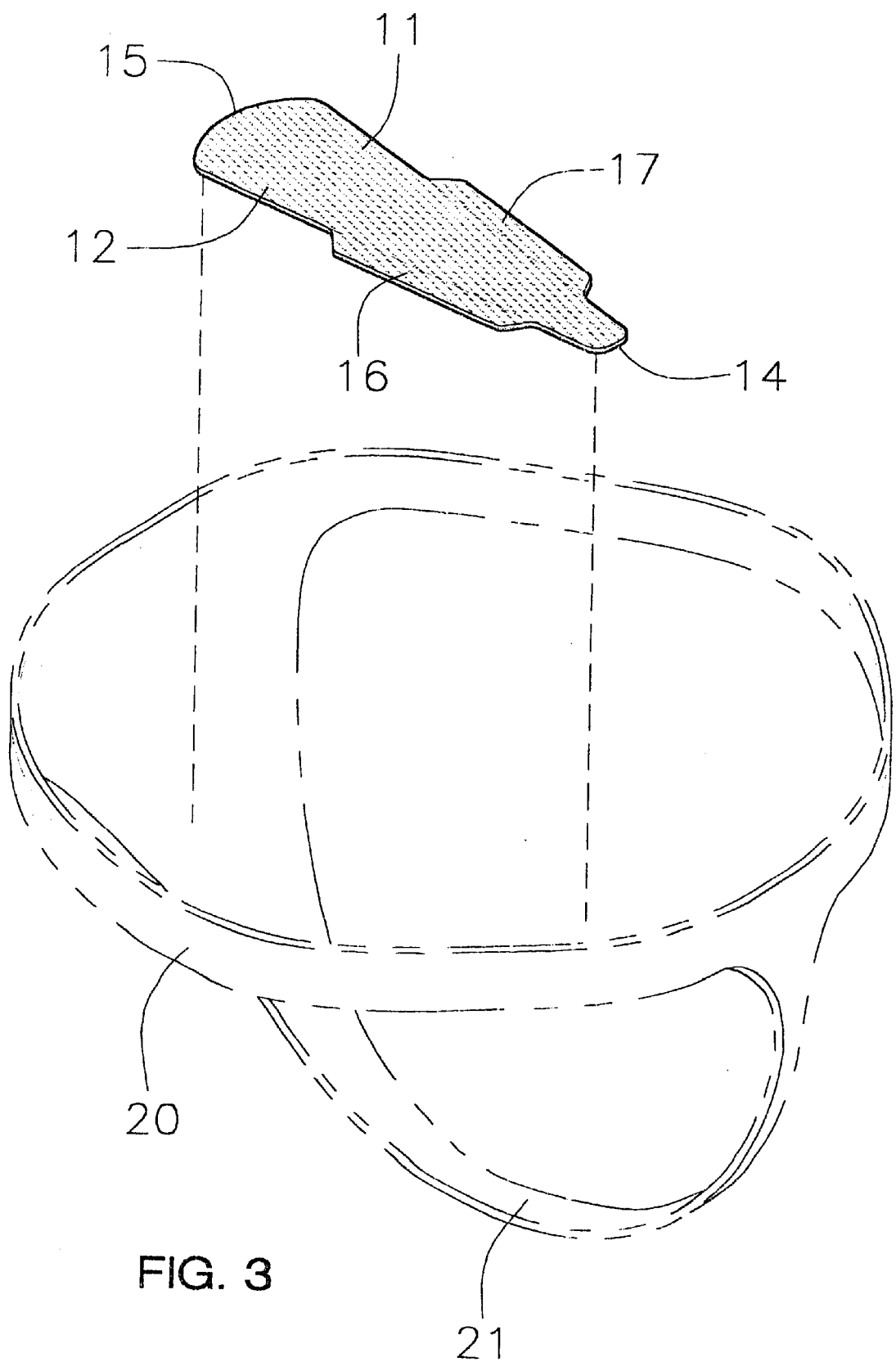
FIG. 3 is a perspective view of the layered piece of material of the present invention being applied to a thong.

With reference now to the drawings, and in particular to FIGS. 1 through 3 thereof, a new thong panty liner embodying the principles and concepts of the present invention and generally designated by the reference numeral 10 will be described.

As best illustrated in FIGS. 1 through 3, the thong panty liner 10 generally comprises a layered piece of material 11 having a top layer 12 and a bottom layer 13 and being adapted to securely fasten to a crotch member 21 of a thong 20. The layered piece of material 11 is tapered from a back edge 15 to a front edge 14 with the back edge 15 being rounded. The bottom layer 13 is made of a moisture-blocking material such as plastic to prevent moisture from seeping therethrough and onto the thong 20. The top layer is made of an absorbent material such as cotton to absorb and hold the moisture. The layered piece of material 11 further includes elongate flap members 16,17 being conventionally and integrally attached along portions of longitudinal edges thereof and being adapted to wrap about the crotch member 21 of the thong 20 to securely hold the layered piece of material 11 to the thong 20. Each of the elongate flap members 16,17 extends from near the front edge 14 of the layered piece of material 11 and terminates approximately midway between the front and back edges 14,15 of the layered piece of material 11. Each of the flap members 16,17 has a straight outer longitudinal edge and slanted end edges. The layered piece of material 11 has a length of approximately 16 centimeters and has a width tapering from approximately 5 centimeters at the back edge 15 to approximately 2 centimeters at the front edge 14.

Adhesive 18 is conventionally disposed upon a bottom of the bottom layer 13 for securely fastening the layered piece of material 11 to the thong 20. The adhesive 18 is also disposed upon the elongate flap members 16,17. A cover member 19 is removably disposed upon the adhesive 18 for the protection thereof. The cover member 19 is shaped to removably cover the layered piece of material 11 including the elongate flap members 16,17.

In use, the user peels the thin cover member 19 off the bottom of the layered piece of material 11 to expose the adhesive 18 and places the layered piece of material 11 upon the crotch member 21 of the thong 20 and wraps the flap members 16,17 about the crotch member 21 to secure the layered piece of material 11 upon the crotch member 21.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, acre deemed readily apparent and obvious to one skilled in the art and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, failing within the scope of the invention.

I claim:

1. A thong panty liner comprising:

a layered piece of material having a top layer and a bottom layer and being adapted to securely fasten to a crotch member of a thong a layered piece of material having a top layer and a bottom layer and being adapted to securely fasten to a crotch member of a thong, said layered piece of material having front, back and longitudinal side edges, said layered piece of material being tapered from said back edge to said front edge with said back edge being rounded, said bottom layer being made of a moisture-blocking material to prevent moisture from seeping therethrough and onto the thong, said top layer being made of an absorbent material to absorb and hold the moisture, wherein said layered piece of material further includes elongate flap members for wrapping about the crotch member of the thong to securely hold said layered piece of material to the thong, said flap members being attached along portions of said longitudinal side edges of said layered piece of material, each of said flap members extending from a point along respective said longitudinal edges near said front edge of said layered piece of material, each of said flap members terminating approximately midway between said front and back edges of said layered piece of material such that said flap member have a longitudinal length that is approximately one half of a longitudinal length of said layered piece of material;

wherein said flap members have a combined width that is less than a width of said layered piece of material at said point along said longitudinal side edges near said front edge of said layered piece of material where each of said flap members extend from near said front edge of said layered piece of material such that said flap members do not overlap when wrapped about the crotch member of the thong;

wherein each of said flap members has a substantially uniform width along a longitudinal length of said flap member;

said layered piece of material having a length of approximately 16 centimeters and having a width tapering from approximately 5 centimeters at said back edge to approximately 2 centimeters at said front edge, adhesive being disposed upon a bottom or said bottom layer of said layered piece of material for securely fastening said layered piece of material to the thong, said adhesive being also disposed upon said elongated flap members; and a cover member being removably disposed upon said adhesive for the protection thereof, said cover member being shaped to removably cover said layered piece of material including said elongated flap members.

* * * * *